United States Patent [19]

Braid

[11] 4,162,225

[45] Jul. 24, 1979

[54] LUBRICANT COMPOSITIONS OF ENHANCED ANTIOXIDANT PROPERTIES

[75] Inventor: Milton Braid, Westmont, N.J.

[73] Assignee: Mobil Oil Corporation, New York, N.Y.

[21] Appl. No.: 897,078

[22] Filed: Apr. 17, 1978

[51] Int. Cl.² ............................................. C10M 1/32
[52] U.S. Cl. .................................... 252/50; 252/401
[58] Field of Search ................................ 252/50, 401

[56] References Cited

U.S. PATENT DOCUMENTS

| | | | |
|---|---|---|---|
| 2,215,591 | 9/1940 | Nelson | 252/50 X |
| 3,222,285 | 12/1965 | Rai et al. | 252/50 X |
| 3,379,779 | 4/1968 | Strobel | 252/401 X |
| 3,413,227 | 11/1968 | Howard et al. | 252/51.5 R |
| 3,597,353 | 8/1971 | Randell et al. | 252/50 |
| 3,697,427 | 10/1972 | Byford et al. | 252/50 X |
| 3,720,616 | 3/1973 | Randell et al. | 252/51.5 R |
| 3,723,316 | 3/1973 | Massie | 252/50 |
| 3,791,803 | 2/1974 | Andress et al. | 252/51.5 R X |
| 3,849,433 | 11/1974 | Butula | 252/51.5 R X |
| 3,926,823 | 12/1975 | Durr et al. | 252/50 X |

*Primary Examiner*—Delbert E. Gantz
*Assistant Examiner*—Andrew Metz
*Attorney, Agent, or Firm*—Charles A. Huggett; Raymond W. Barclay; Thomas S. Szatkowski

[57] ABSTRACT

Lubricant compositions containing oleaginous materials and, in amounts sufficient to impart resistance to oxidation thereto, adducts of benzotriazole compounds and substituted acrylonitrile.

6 Claims, No Drawings

LUBRICANT COMPOSITIONS OF ENHANCED ANTIOXIDANT PROPERTIES

BACKGROUND OF THE INVENTION

This invention relates to oleaginous compositions normally susceptible to oxidative deterioration. In particular, the invention relates to compositions such as mineral and synthetic lubricating oils, gear oils, transmission fluids and other oleaginous compositions which normally require the presence of antioxidant additives.

DESCRIPTION OF THE PRIOR ART

Prior to the present invention, triazoles have been employed in lubricant compositions as metal deactivators. For example, U.S. Pat. No. 3,597,353 of Randell et al discloses the use of 4,5,6,7-tetrahydrobenzotriazole as a metal deactivating additive for natural and synthetic lubricants. Similarly, U.S. Pat. No. 3,413,227 of Howard et al teaches that an alkyl-substituted benzotriazole where the alkyl group contains from 2 to 20 carbon atoms can be used as a corrosion or tarnish inhibitor.

In U.S. Pat. No. 4,060,491 Bridger et al teach the utilization of 5-alkyl-benzotriazoles, in which the alkyl group contains from 4 to 16 carbon atoms, in a method for reducing wear between moving steel-on-steel surfaces.

In U.S. Pat. No. 3,788,993 of Andress, it is taught that benzotriazoles react with alkyl-or alkenylsuccinic anhydrides to form products which impart corrosion inhibiting properties to lubricating oils.

Nnadi et al, in U.S. Pat. No. 4,048,082, discloses that esters of adducts of benzotriazole and unsaturated dicarboxylic acids or anhydrides thereof impart anti-rust properties to organic compositions.

None of the prior art patents disclose the adducts of benzotriazole and substituted acrylonitrile of the present invention.

SUMMARY OF THE INVENTION

It is now been found that adducts of a benzotriazole compound and a substituted acrylonitrile, which have the formula;

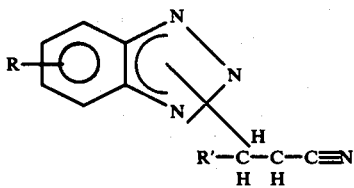

where R is hydrogen or a hydrocarbyl group containing from 1 to about 12 carbon atoms, and R' is hydrogen or an alkyl group containing from 1 to 8 carbon atoms, impart improved oxidation resistance to the oleaginous compositions to which they are added.

Referring to the above formula, the preferred adducts are those in which R is hydrogen or an alkyl group containing from 1 to about 8 carbon atoms and R' is hydrogen or an alkyl group containing from 1 to about 4 carbon atoms.

Particularly preferred are those adducts in which R is hydrogen, methyl or n-butyl and R' is hydrogen or methyl.

Of particular significance, in accordance with the present invention is the ability to improve the resistance to oxidation of oleaginous materials such as lubricating media which may comprise liquid oils, in the form of either a mineral or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weight of these oils may range from about 250 to about 800. Where the lubricant is to be employed in the form of grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorous-containing acids, liquid ureas, ferrocene derivative, hydrogenated mineral oils, chain-type polyphenyls, siloxanes and silicones (polysiloxanes), alkyl-substituted diphenyl ethers typified by a butyl-substituted bis(b-phenoxy phenyl)ether, phenoxy phenylethers.

It is to be understood, however, that the compositions contemplated herein can also contain other materials. For example, corrosion inhibitors, extreme pressure agents, viscosity index agents, co-antioxidants, anti-wear agents, anti-rust agents and the like can be used. These materials do not detract from the value of the compositions of this invention rather these materials serve to impart customary properties to the particular compositions in which they are incorporated. Mineral oil heat exchange fluids particularly contemplated in accordance with the present invention have the following characteristics: high thermal stability, high initial boiling point, low viscosity, high heat-carrying ability and low corrosion tendency.

The transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions". Specifications for low-temperature and aircraft fluids are defined in the U.S. Government Specification MIL-H-5606A.

In addition, the oxidation resistance of functional fluids such as hydraulic fluids can be improved by the adducts of the present invention.

The adducts of the present invention may be employed in the oleaginous material any amount which is effective for imparting the desired degree of oxidation resistance thereto. In many applications, however, the additive is effectively employed in amounts from 0.01 to 10% by weight, and preferably from 0.1 to 5% of the total weight of the composition.

The adducts of the present invention are formed by reacting a benzotriazole compound with substituted acrylonitrile.

In general, benzotriazole compounds which may be used to form the adducts of the present invention have the formula:

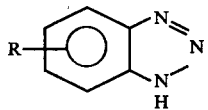

where R is hydrogen or a hydrocarbyl group containing from 1 to 12 carbon atoms.

Preferred are those materials in which R is hydrogen or an alkyl group containing from 1 to about 8 carbon atoms. Particularly preferred are benzotriazole, toluotriazole and 5-n-butylbenzotriazole.

Substituted acrylonitrile compounds which are reacted with the benzotriazole materials described above to form the adducts utilized in the composition of this invention have the formula

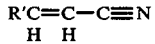

where R' is hydrogen or an alkyl group containing from 1 to about 8 carbon atoms such as: methyl, propyl, butyl, amyl, hexyl, etc. Preferred are those acrylonitriles where R' is hydrogen or methyl.

In general, these compounds are reacted in mole ratios of benzotriazole/acrylonitrile of about 0.5 to about 2.5, with from 1 to about 2 being preferred. The reaction proceeds at a temperature from about 25° C. to about 150° C. with from about 90° C. to about 125° C. being preferred. Reaction times are from about 0.25 to about 16 hours.

The reaction is catalyzed by either acidic or basic materials. Suitable acidic catalysts include hydrogen chloride, p-toluenesulfonic acid, acetic acid, phosphoric acid, boron trifluoride, boron trifluoride etherate, etc. Preferred are hydrogen chloride and p-toluenesulfonic acid. Suitable basic catalysts include sodium methoxide, sodium ethoxide, potassium isopropoxide, potassium tert-butoxide, aluminum isopropoxide, etc. Preferred are sodium ethoxide and potassium tert-butoxide.

DESCRIPTION OF SPECIFIC EMBODIMENTS

The following examples and comparative data will serve to illustrate the marked improvement in oxidation resistance of oleaginous materials, containing adducts of benzotriazole and acrylonitrile. It will be understood, however, that it is not intended that the invention be limited to the particular compositions containing those adducts described herein. Various modifications of those compositions can be employed, as will be readily apparent to those skilled in the art.

EXAMPLE 1

Addition to Benzotriazole to Acrylonitrile—Base Catalyzed

A mixture of 23 g. of benzotriazole and 10.6 g. of acrylonitrile was heated on a steam bath until the reaction mixture became homogeneous. To the solution, 0.1 g. of potassium tert-butoxide was added, and after one hour, an additional 10.6 g. of acrylonitrile was added to replace evaporation losses. The resulting mixture was heated in a boiling water bath under reflux conditions for 5 hours. Gas chromatography indicated a 90% conversion of the benzotriazole to addition product. An analytical example of the addition product was crystallized from carbon tetrachloride after removal of excess acrylonitrile. The white solid had m.p. 83°–84° C.

| Elemental Analysis (Wt. %) | C | H |
|---|---|---|
| Calculated for $C_9H_8N_4$ | 62.78 | 4.68 |
| Found | 62.27 | 4.68 |

A less pure addition product obtained from the reaction product by a single crystallization from benzene, m.p. 63°–66° C., was satisfactory for intended applications.

EXAMPLE 2

Addition of Benzotriazole to Acrylonitrile—Acid Catalyzed

Hydrogen chloride gas was passed subsurface into a mixture of 59.9 g of benzotriazole and 100 ml. of toluene heated at 50° C. while stirring for several minutes. The temperature was raised to 100° C., 53.1 g of acrylonitrile was added during 2 hours, and stirring at 100° C. was continued for an additional 5 hours. Gas chromatography showed that substantial conversion to a reaction product had occurred. To the reaction mixture, 0.1 g of p-toluenesulfonic acid was added and reaction at 100° C. was continued for a total of 24 hours more. The reaction mixture was treated with 100 ml. of 30% sodium carbonate aqueous solution and extracted with benzene. The addition product was obtained from the residue after distillation of solvent from the benzene extract by crystallization from 2-proponal. Recrystallization from benzene gave a white solid m.p. 83°–84° C.

| Elemental Analysis (Wt. %) | C | H | N |
|---|---|---|---|
| Calculated for $C_9H_8N_4$ | 62.78 | 4.68 | 32.54 |

| Elemental Analysis (Wt. %) | C | H | N |
|---|---|---|---|
| Found | 63.29 | 4.99 | 32.2 |

EXAMPLE 3

Attempted Addition of Benzotriazole to Acrylonitrile—Uncatalyzed

A mixture of 59.5 g of benzotriazole, 53.1 g of acrylonitrile, and 100 ml. of benzene was heated with refluxing at 70° C. for about 12 hours. Benzene and unreacted acrylonitrile were removed by rotary film evaporation. The residue, a white solid, weighed 58.1 g, and was shown by its infrared spectrum to be essentially benzotriazole. This example shows that uncatalyzed addition, if it occurs at all, is impractically slow.

The adducts of Examples 1 and 2 were then tested for oxidation inhibition activity. For the oxidation test, the adducts were blended into a neutral solvent refined oil base oil having a viscosity at 100° F. of 130 SUS. The oils were then subjected to a stream of air at the rate of 5 liters per hour at a temperature of 325° F. for 40 hours in the presence of metals having pro-oxidant properties: iron, copper, lead and aluminum. The lead sample is weighed before and after the test, since lead is one of the metals more susceptible to corrosion by oxidation. The test measurements are change in acidity or neutralization number (ΔNN) as measured by ASTM D-974, change in kinematic viscosity at 210° F. (ΔKV), lead loss in milligrams and sludge. Results of the test are presented in Table 1.

TABLE 1

Catalytic Oxidation Test, Mineral Oil, 325° F., 40 hours.

| Base Oil | ΔNN | ΔKV | Pb Loss, Mg | Sludge |
|---|---|---|---|---|
| Base oil without additive | 17 | 334 | 66 | Heavy |
| Adduct of Example 1 | | | | |
| Base Oil + 1 wt % adduct | 12.7 | 209 | 63.4 | Mod. |
| Base Oil + 0.5 wt % adduct | 11.3 | 263 | 133.2 | Light |
| Base Oil + 0.25 wt % adduct | 11.1 | 309 | 237.3 | Mod. |
| Adduct of Example 2 | | | | |
| Base Oil + 1 wt % adduct | 8.9 | 140 | 136.2 | Light |
| Base Oil + 0.5 wt % adduct | 8.6 | 108 | 32.8 | Mod. |

TABLE 1-continued

Catalytic Oxidation Test, Mineral Oil, 325° F., 40 hours.

| Base Oil | ΔNN | ΔKV | Pb Loss, Mg | Sludge |
|---|---|---|---|---|
| Base Oil + 0.25 wt % adduct | 9.4 | 122 | 33.9 | Mod. |

The data presented in the above table shows that the oxidative stability of the base oil is improved by the addition of the adducts of benzotriazole and acrylonitrile.

I claim:

1. A lubricant composition which comprises an oleaginous material and, in an amount effective to impart oxidation properties thereto, an adduct having the formula:

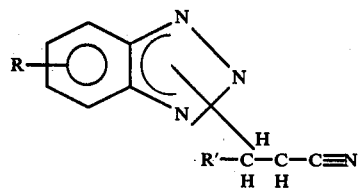

where R is selected from the group consisting of hydrogen and hydrocarbyl containing from 1 to about 12 carbon atoms, and R' is selected from the group consisting of hydrogen and alkyl containing from 1 to about 8 carbon atoms.

2. The composition of claim 1 wherein R is selected from the group consisting of hydrogen and alkyl containing from 1 to about 8 carbon atoms and R' is selected from the group consisting of hydrogen and alkyl containing from 1 to about 4 carbon atoms.

3. The composition of claim 1 wherein R is selected from the group consisting of hydrogen, methyl and n-butyl, and R' is selected from the group consisting of hydrogen and methyl.

4. The composition of claim 1 wherein said oleaginous material is selected from the group consisting of mineral oils, synthetic oils and greases thereof.

5. The composition of claim 1 wherein said adduct is present in an amount of from about 0.01 to about 10 weight percent of the total composition.

6. The composition of claim 1 wherein said adduct is present in an amount of from about 0.1 to 5 weight percent of the total composition.

* * * * *